하지 않음

(12) United States Patent
Matsusue

(10) Patent No.: US 12,404,390 B2
(45) Date of Patent: *Sep. 2, 2025

(54) FILM MOLDING COMPOSITION AND FILM

(71) Applicant: Shin—Etsu Chemical Co., Ltd., Tokyo (JP)

(72) Inventor: Shintaro Matsusue, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 381 days.

This patent is subject to a terminal disclaimer.

(21) Appl. No.: 17/638,790

(22) PCT Filed: Sep. 3, 2020

(86) PCT No.: PCT/JP2020/033419
§ 371 (c)(1),
(2) Date: Feb. 25, 2022

(87) PCT Pub. No.: WO2021/045151
PCT Pub. Date: Mar. 11, 2021

(65) Prior Publication Data
US 2024/0034859 A1  Feb. 1, 2024

(30) Foreign Application Priority Data
Sep. 4, 2019 (JP) ................. 2019-161360

(51) Int. Cl.
C08L 1/28 (2006.01)
A61K 9/48 (2006.01)
C08J 5/18 (2006.01)

(52) U.S. Cl.
CPC ............ C08L 1/284 (2013.01); A61K 9/4891 (2013.01); C08J 5/18 (2013.01); C08J 2301/28 (2013.01); C08L 2203/16 (2013.01)

(58) Field of Classification Search
CPC ... C08L 1/284; C08L 2203/16; C08J 2301/28; A23P 20/105; A23L 29/262; A61K 47/38; A61K 9/5047
See application file for complete search history.

(56) References Cited

U.S. PATENT DOCUMENTS

| | | | | |
|---|---|---|---|---|
| 6,753,330 B2 * | 6/2004 | Takano | ................ | A61P 29/00 514/247 |
| 2010/0144807 A1 * | 6/2010 | Takaishi | .............. | A61P 3/06 514/370 |
| 2017/0173160 A1 * | 6/2017 | Yamashita | ............. | C08L 1/28 |
| 2018/0015045 A1 | 1/2018 | Maruyama | | |
| 2018/0282435 A1 * | 10/2018 | Matsusue | ............ | C08B 1/06 |
| 2019/0175617 A1 | 6/2019 | Westrin | | |
| 2021/0196640 A1 | 7/2021 | Osaki et al. | | |

FOREIGN PATENT DOCUMENTS

| | | | | |
|---|---|---|---|---|
| CN | 101927003 A | 12/2010 | | |
| CN | 106727401 A | 5/2017 | | |
| CN | 106883461 A | 6/2017 | | |
| CN | 111377746 A | * 7/2020 | ............ | C04B 35/10 |
| EP | 0714656 A1 | 6/1996 | | |
| EP | 2017289 A1 | * 1/2009 | .......... | A61K 31/717 |
| JP | 08208458 A | 8/1996 | | |
| JP | 2010270039 A | 2/2010 | | |
| JP | 2017533231 A | 11/2017 | | |
| WO | 2003011257 A1 | 2/2003 | | |
| WO | 2014018279 A1 | 1/2014 | | |
| WO | 2018008660 A1 | 1/2018 | | |

OTHER PUBLICATIONS

Adden et al., Analysis of the Substituent Distribution in the Glucosyl Units and Along the Polymer Chain of Hydroxymethyl Celluloses with Statistical Evaluation. Cellulose 13:459-476 (Year: 2006).*
Brogley et al. Determination of the Chemical Structure of Cellulose Based Polymers. ARPN Journal of Engineering and Applied Sciences, vol. 11m No. 11 (Year: 2016).*
Kostryukov et al. Hydrolysis of HPMC by trifluoromethanesulfonic acid and Subsequent Determination of Chemical Structure by NMR. Polymer Science B, vol. 62, No. 3, pp. 279-289 (Year: 2020).*
Perez et al. Dynamics of Adsorption of HPMC at the Air-Water Interface. Food Hydrocolloids, 22, pp. 687-402 (Year: 2008).*
Teruya et al. A Single Subcutaneous Injection of Cellulose Ethers Administered Long before Infection Confers Sustained Protection against Prion Diseases. Plos Pathog 12(12) 1006045 pp. 1-23 (Year: 2016).*
Extended European Search report completed Jul. 25, 2023.
CN Office action dated Sep. 8, 2023, App. No. 202080061967.4.
Search Report for International Application PCT/JP2020033419 dated Oct. 13, 2020.

* cited by examiner

Primary Examiner — Katarzyna I Kolb

(57) ABSTRACT

[Problems] A composition capable of forming a film having both good solubility and good strength, and the film are provided.
[Solution] The composition includes first hydroxypropyl methyl cellulose (HPMC) polymer having a viscosity of 2.5-4.5 mPa·s, second HPMC polymer having 6.0-50.0 mPa·s, third HPMC polymer having 4.5-15.0 mPa·s, a gelling agent, and a solvent, each viscosity determined at 20° C. in a 2 mass % aqueous solution, wherein the first HPMC polymer is selected from three members: HPMC-IA in Group I and HPMC-IIA and HPMC-IIB in Group II, the second HPMC polymer is the same member as that of the first HPMC polymer, provided that DS (MS) of the second HPMC polymer may be the same as or different from the DS (MS) of the first HPMC polymer, and the third HPMC polymer is selected from a member or members in a Group different from the Group of the first HPMC polymer.

8 Claims, 1 Drawing Sheet

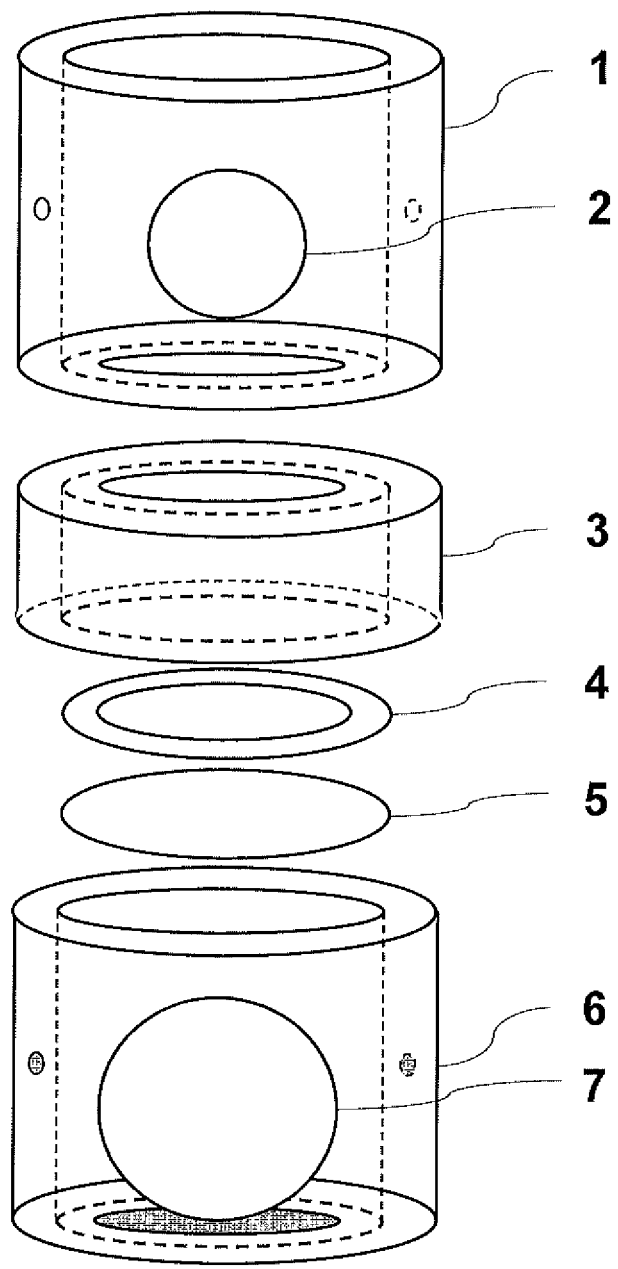

FILM MOLDING COMPOSITION AND FILM

CROSS-REFERENCE TO RELATED APPLICATIONS

The present application is a National Stage application of and claims priority to PCT application PCT/JP2020/033419 filed Sep. 3, 2020, which claims priority benefit to Japanese Application No. 2019-161360, filed on Sep. 4, 2019, the contents of the above applications are incorporated by reference herein in their entireties for all purposes.

TECHNICAL FIELD

The invention relates to a composition for forming a film, and the film.

BACKGROUND ART

A water-soluble cellulose ether such as hydroxypropyl methyl cellulose (also referred to herein as "HPMC") is widely used in pharmaceutical and food applications. Among examples of the water-soluble cellulose ether, HPMC is particularly excellent in solubility in water, and forms a tough and flexible film by drying the aqueous HPMC solution. Since the formed film has high transparency and is excellent in gas barrier properties and moisture barrier properties, it is widely used as a film-forming base material for coating tablets and granules, and as a base material for a film formulation and a hard capsule.

A hard capsule is a conventionally widely used dosage form because it is easy to formulate and can mask the taste and odor of the capsule content. Gelatin has been widely used as a base material for the hard capsule. However, since gelatin is derived from animals, there is a risk of infection such as bovine spongiform encephalopathy (BSE). In addition, the gelatin tends to crack when the moisture content decreases. For this reason, a hard capsule produced from the gelatin as a base material must contain a large amount of moisture. As a result, a drug may be deactivated due to the moisture.

On the other hand, the water-soluble cellulose ether is derived from a plant, and even if the moisture content in the film is lowered, the strength of the film does not decrease. Thus, the water-soluble cellulose ether has no problem described above.

A hard capsule produced from a water-soluble cellulose ether as a base material has many advantages as described above, but it has problems that solubility in water is low compared with the hard capsules produced from a gelatin as a base material and release of the hard capsule content is delayed.

For the purpose of improving the solubility of a hard capsule produced from a water-soluble cellulose ether as a base material, it is described in Patent Document 1 that a film composition for a capsule comprises 18 to 28 parts by weight of HPMC having a viscosity at 20° C. of from 2.4 to 5.4 cSt, as determined in a 2% aqueous solution, as a base material; 0.01 to 0.1 parts by weight of carrageenan as a gelling agent; and 0.05 to 0.6 parts by weight of potassium ions, calcium ions or both, as a gelling aid. It is also described in Patent Document 2 that a film for a hard capsule comprises hypromellose and at least one selected from the group consisting of monosaccharides, disaccharides and starches.

PRIOR ART DOCUMENT

Patent Document

Patent Document 1: JPH08-208458A
Patent Document 2: JP 2010-270039A

SUMMARY OF THE INVENTION

Problem to be solved by the Invention

However, a film formed from HPMC providing a relatively low viscosity, such as HPMC described in Patent Document 1, is fragile and has insufficient strength. An additive such as monosaccharides, disaccharides and starches, as described in Patent Document 2, has a possibility of inducing rapid microbial growth.

In view of the above circumstances, an object of the invention is to provide a film-forming composition capable of forming a film having both good solubility and good strength, as well as the film.

Solution to the Problem

As a result of extensive studies to achieve the above object, the inventors have found that a film excellent in solubility and strength can be formed by combining first and second HPMC polymers having different viscosities with a HPMC polymer having a substitution degree different from those of the first and second HPMC polymers, as water-soluble cellulose ethers, and thus has completed the invention.

In an aspect of the invention, there is provided a composition for forming a film, the composition comprising:
  a first HPMC polymer having a viscosity at 20° C. of from 2.5 to 4.5 mPa·s, as determined in a 2% by mass aqueous solution;
  a second HPMC polymer having a viscosity at 20° C. of from 6.0 to 50.0 mPa·s, as determined in a 2% by mass aqueous solution;
  a third HPMC polymer having a viscosity at 20° C. of from 4.5 to 15.0 mPa·s, as determined in a 2% by mass aqueous solution;
  a gelling agent; and
  a solvent;
wherein the first HPMC polymer is selected from three members:
  one member in Group I:
    HPMC-IA having a degree of substitution (DS) of methoxy groups of from 1.80 to 2.00 and a molar substitution (MS) of hydroxypropoxy groups of from 0.20 to 0.34, and
  two members both in Group II:
    HPMC-IIA having a degree of substitution (DS) of methoxy groups of from 1.10 to 1.60 and a molar substitution (MS) of hydroxypropoxy groups of from 0.10 to 0.33, and
    HPMC-IIB having a degree of substitution (DS) of methoxy groups of from 1.80 to 2.00, and a molar substitution (MS) of hydroxypropoxy groups of from 0.40 to 0.70,
wherein the second HPMC polymer is the same member as that of the first HPMC polymer, provided that the DS of the second HPMC polymer may be the same as or different from the DS of the first HPMC polymer, and the MS of the second HPMC polymer may be the same as or different from the MS of the first HPMC polymer, and wherein the third HPMC polymer is selected from a member or members in a Group different from the Group of the first HPMC polymer.

In another aspect of the invention, there is provided a film comprising the first HPMC polymer, the second HPMC polymer, the third HPMC polymer and a gelling agent.

Effect of the Invention

According to the invention, a film excellent in solubility can be obtained while maintaining film strength. In addition, since the later-described dispersion viscosity of the composition for forming a film can be reduced, the film can be efficiently produced.

BRIEF DESCRIPTION OF DRAWINGS

FIG. 1 shows a sample holder to be used for measuring the dissolution time of a film.

MODE FOR CARRYING OUT THE INVENTION

At first, HPMC polymers to be used in a composition for forming a film will be described.

First, second and third HPMC polymers, which are nonionic, are used for the composition for forming a film.

<Viscosity of Each HPMC Polymer>

The strength and solubility of the HPMC film are correlated with the viscosity at 20° C. of the 2% by mass aqueous solution of HPMC. When the viscosity of HPMC is too low, the solubility of HPMC film is improved, but the strength of HPMC film is lowered. On the contrary, when the viscosity of HPMC is too high, the strength of HPMC film is improved, but the solubility of HPMC film is lowered. Accordingly, the viscosities of the first, second and third HPMC polymers to be used in the composition for forming a film must be within the ranges described later.

The viscosity at 20° C. of the 2% by mass aqueous solution of the first HPMC polymer is from 2.5 to 4.5 mPa·s, preferably from 2.8 to 4.5 mPa·s, more preferably from 3.0 to 4.5 mPa·s. When the viscosity is less than 2.5 mPa·s, the strength of the film decreases, causing problems such as easy cracking of the film. When the viscosity is more than 4.5 mPa·s, it becomes difficult to obtain good solubility of the film.

The viscosity at 20° C. of the 2% by mass solution of the second HPMC polymer is from 6.0 to 50.0 mPa·s, preferably from 6.0 to 40.0 mPa·s, more preferably from 6.0 to 35.0 mPa·s. When the viscosity is less than 6.0 mPa·s, since the content of the cellulose ether having a low viscosity increases, the strength of the film decreases, causing problems such as easy cracking of the film. When the viscosity is more than 50.0 mPa·s, it is difficult to obtain good solubility of the film.

The viscosity at 20° C. of the 2% by mass aqueous solution of the third HPMC polymer is from 4.5 to 15.0 mPa·s, preferably from 4.5 to 14.5 mPa·s, more preferably from 4.5 to 14.0 mPa·s. When the viscosity is less than 4.5 mPa·s, there are problems such as the decreased strength and easy cracking of the film. When the viscosity is more than 15.0 mPa·s, it is difficult to obtain good solubility of the film.

In addition, the difference between the viscosity at 20° C. of a 2% by mass aqueous solution of the first HPMC polymer and that of the second HPMC polymer, i.e., (the viscosity at 20° C. of the 2% by mass aqueous solution of the second HPMC polmer)−(the viscosity at 20° C. of the 2% by mass aqueous solution of the first HPMC polymer), is preferably 2.0 mPa·s or more, more preferably from 2.3 to 47.0 mPa·s, and still more preferably from 2.5 to 45.0 mPa·s, from the viewpoint of solubility of the film.

Since the viscosity at 20° C. of the 2% by mass aqueous solution of each of the first, second and third HPMC polymers is less than 600 mPa·s, the viscosity may be determined using the Ubbelohde type viscometer in accordance with the viscosity measurement by capillary tube viscometer of the General Tests in the Japanese Pharmacopoeia Seventeenth Edition.

<Substitution Degrees of Each HPMC Polymer>

Next, the substitution degrees of HPMC polymers to be used in the composition for forming a film will be described.

The first HPMC polymer is selected from three members in Groups I and II. The second HPMC polymer is the same member as that of the first HPMC, provided that the DS of the second HPMC may be the same as or different from the DS of the first HPMC, and the MS of the second HPMC may be the same as or different from the MS of the first HPMC. The third HPMC polymer is selected from a member or members in a Group different from the Group of the first HPMC polymer.

By using the first and second HPMC polymers which are the same members in the same Group, have different viscosities and may have the same or different substitution degrees, the solubility of the film is improved. By adding a third HPMC which is a member in the different Group from the Group of the first and second HPMC polymers, the solubility of the film can be further improved and the later-described dispersion viscosity of the composition for forming a film can be reduced.

Group I of HPMC consists of one member providing excellent strength of film.

More specifically, Group I consists of HPMC-IA having a degree of substitution (DS) of methoxy groups of from 1.80 to 2.00, preferably from 1.83 to 1.97, more preferably from 1.85 to 1.95, and a molar substitution (MS) of hydroxypropoxy groups of from 0.20 to 0.34, preferably from 0.22 to 0.30.

Group II of HPMC consists of two members providing excellent solubility of film.

More specifically, Group II consists of HPMC-IIA having a degree of substitution (DS) of methoxy groups of from 1.10 to 1.60, preferably from 1.30 to 1.60, more preferably from 1.35 to 1.55, and a molar substitution (MS) of hydroxypropoxy groups of from 0.10 to 0.33, preferably from 0.20 to 0.30; and HPMC-IIB having a degree of substitution (DS) of methoxy groups of from 1.80 to 2.00, preferably from 1.83 to 1.97, more preferably from 1.83 to 1.95, and a molar substitution (MS) of hydroxypropoxy groups of from 0.40 to 0.70, preferably from 0.45 to 0.65.

The combinations of the members as the first, second and third HPMC polymers include, as this order of combination in parentheses, (IA, IA, IIA), (IA, IA, IIB), (IIA, IIA, IA), and (IIB, IIB, IA). The respective parentheses are expressed as "(member of the first HPMC polymer, member of the second HPMC polymer, member of the third HPMC polymer)". The combination is preferably (IA, IA, IIA) or (IA, IA, IIB), more preferably (IA, IA, IIA), from the viewpoint of strength or solubility of the film.

The second HPMC polymer is the same member as that of the first HPMC polymer, and may have the same or different substitution degrees, i.e., may have the degree of substitution (DS) of methoxy groups same as or different from that of the first HPMC and the molar substitution (MS) of hydroxypropoxy groups same as or different from that of the first HPMC. The second HPMC polymer having the same substitution degrees (i.e., same DS and MS) as those of the first HPMC polymer can be obtained by adjusting the viscosity of the second HPMC polymer to a desired viscosity that differs from that of the first HPMC polymer, e.g., by changing the degree of depolymerization. The second HPMC polymer is preferably the same member and has the same substitution degrees as those of the first HPMC polymer, from the viewpoint of easy adjustment of viscosity through depolymerization.

A degree of substitution (DS) of the methoxy groups and a molar substitution (MS) of the hydroxypropoxy groups in HPMC may be determined by converting the values measured in accordance with the assay for measuring the substitution degrees of "Hypromellose" in the Japanese Pharmacopoeia Seventeenth Edition.

<Properties of HPMC Mixture>

The first, second and third HPMC polymers are blended to obtain a HPMC mixture preferably having the following properties, so that a composition containing the mixture can form a film excellent in solubility and others.

A degree of substitution (DS) of the methoxy groups of the HPMC mixture of the first, second and third HPMC polymers is preferably from 1.50 to 2.00, more preferably from 1.55 to 1.98, still more preferably from 1.60 to 1.96, and particularly preferably from 1.65 to 1.90, from the viewpoint of strength or solubility of the film.

A molar substitution (MS) of the hydroxypropoxy groups of the HPMC mixture of the first, second and third HPMC polymers is preferably from 0.20 to 0.55, more preferably from 0.21 to 0.50, still more preferably from 0.22 to 0.45, and particularly preferably from 0.22 to 0.35, from the viewpoint of solubility or flexibility of the film.

The degree of substitution (DS) of the methoxy groups and the molar substitution (MS) of the hydroxypropoxy groups of the HPMC mixture of the first, second and third HPMC polymers may be determined by converting values measured in accordance with the assay of measuring the substitution degrees of "Hypromellose" in the Japanese Pharmacopoeia Seventeenth Edition.

The viscosity at 20° C. of the 2% by mass aqueous solution of the HPMC mixture of the first, second and third HPMC polymers is preferably from 3.0 to 15.0 mPa·s, more preferably from 3.5 to 12.0 mPa·s, still more preferably from 4.0 to 10.0 mPa·s, and particularly preferably from 4.0 to 7.0 mPa·s, from the viewpoint of strength of the film or film thickness control.

Since the viscosity at 20° C. of the 2% by mass aqueous solution of the HPMC mixture of the first, second and third HPMC polymers is less than 600 mPa·s, the viscosity may be determined using a Ubbelohde type viscometer in accordance with the viscosity measurement by capillary viscometer of the General Tests in the Japanese Pharmacopoeia Seventeenth Edition.

A dispersion viscosity is a viscosity at 50° C. of a 20% by mass dispersion containing water as a solvent. The dispersion viscosity of the HPMC mixture of the first, second and third HPMC polymers is preferably from 2000 to 15000 mPa·s, more preferably from 2300 to 13000 mPa·s, still more preferably from 2600 to 11000 mPa·s, and particularly preferably from 2600 to 6300 mPa·s, from the viewpoint of productivity of the film.

The dispersion viscosity of the HPMC mixture of the first, second and third HPMC polymers may be measured, for example, by a rheometer MCR301 produced by Anton Paar GmbH.

First, an aluminum measuring cup (C-CC27) and a blade type jig (ST24-2D/2V/2V-30) are adjusted to 80° C. in advance, and 7 g of HPMC to be used for the composition for forming a film and hot water of 98° C. are mixed thoroughly in the measuring cup to prepare a 20% by mass dispersion of HPMC to be used for the composition for forming a film. The blade type jig is set in the measuring section, and the measuring cup is capped with a plastic lid in order to prevent evaporation of the solvent. After being left to stand at 80° C. for 5 minutes for defoaming, the dispersion is stirred at 180 rpm at 60° C. for 4 minutes, and then the temperature is lowered to 50° C. at a rate of 0.5° C./min while stirring at 60 rpm. The shear viscosity when arriving at 50° C. is defined as the dispersion viscosity of HPMC to be used in the composition for forming a film. The temperature of the sample measuring section is controlled by Peltier temperature control, and data are collected at two points per minute. The measurement is repeated three times, and the average value thereof is defined as the dispersion viscosity of HPMC to be used in the composition for forming a film.

<Content of Each HPMC Polymer>

When the first, second and third HPMC polymers are blended to obtain a HPMC mixture having the above-described properties, a preferred content of each HPMC polymer in the composition for forming a film will be described. The first, second and third HPMC polymers may be blended in advance and then mixed with the other component or components in the composition for forming a film. Alternatively, the other component or components may be mixed with one or more of HPMC polymers.

The content of the first HPMC polymer in the composition for forming a film is preferably from 2.0 to 15.0% by mass, more preferably from 2.0 to 13.0% by mass, from the viewpoint of strength or solubility of the film.

The content of the second HPMC polymer in the composition for forming a film is preferably from 0.5 to 7.0% by mass, more preferably from 0.8 to 6.5% by mass, from the viewpoint of strength of the film or film thickness control.

The content of the third HPMC polymer in the composition for forming a film is preferably from 4.0 to 18.0% by mass, more preferably from 4.5 to 15.5% by mass, from the viewpoint of solubility of the film.

<How to Obtain Each HPMC Polymer>

The first, second and third HPMC polymers may be produced by known methods. They may be produced, for example, by the following method.

An HPMC polymer may be produced by a method comprising steps of: bringing cellulose pulp into contact with an alkali metal hydroxide solution such as an aqueous sodium hydroxide solution to obtain alkali cellulose, reacting the alkali cellulose with an etherifying agent such as methyl chloride or propylene oxide at 60 to 100° C. to obtain a reaction product, and washing, drying and pulverizing the reaction product. Finally, the method for producing an HPMC polymer may comprise an optional step of depolymerizing the obtained HPMC polymer, for example, in the presence of an acid such as hydrochloric acid at 50 to 95° C. for 20 to 120 minutes for reduction of the viscosity to obtain an HPMC polymer having desired substitution degrees and viscosity.

Commercially available products may be used as the first, second, and third HPMC polymers.

<Gelling Agent>

Next, a gelling agent to be used in the composition for forming a film will be described.

The gelling agent is not particularly limited as long as the composition for forming a film can gel at about room temperature (15 to 35° C.). Examples of the gelling agent may include kappa carrageenan (k-carrageenan), iota carrageenan (i-carrageenan), gellan gum, pectin, curdlan, agar, and tamarind gum. The gelling agent may be used optionally in combination of two or more types. A commercially available gelling agent may be used as the gelling agent.

The content of the gelling agent in the composition for forming a film is preferably from 0.04 to 1.0% by mass, more preferably from 0.05 to 0.8% by mass, from the viewpoint of solubility of the film or film thickness control.

<Solvent>

Next, a solvent to be used in the composition for forming a film will be described.

The solvent is not particularly limited as long as the solvent can dissolve HPMC and the gelling agent. Examples of the solvent include water and a mixed solvent of water and a lower alcohol having 1 to 4 carbon atoms. A commercially available solvent may be used as the solvent. The solvent may be used optionally in combination of two or more types. As the solvent to be used in the composition for forming a film, water is preferred from the viewpoint of safety and environmental aspects.

Examples of the lower alcohol having 1 to 4 carbon atoms to be used as the mixed solvent of water and the lower alcohol include methanol, ethanol, and propanol. The content of water in the mixed solvent is not particularly limited. It is preferably from 20.0 to 99.9% by mass in the total mass of the mixed solvent from the viewpoint of maintaining uniformity of the composition for forming a film.

The content of the solvent to used in the composition for forming a film is preferably from 59.0 to 93.46% by mass, more preferably from 70.0 to 88.0% by mass, from the viewpoint of controlling the film thickness.

<Additive Other Than Gelling Agent>

The composition for forming a film may comprise an optional additive other than the gelling agent. Examples of the optional additive include a gelling aid, a plasticizer, a pigment, a flavoring agent, and an antifoaming agent. It is preferable that the composition for forming a film contain no water-soluble cellulose ether other than the first, second and third HPMC polymers described above. The additive other than the gelling agent is preferably added in such a manner to be uniformly dissolved or dispersed in the composition for forming a film. The additive other than the gelling agent may be used optionally in combination of two or more types. A commercially available additive may be used as the additive other than the gelling agent.

Examples of the gelling aid include a substance containing a cation such as potassium ion, calcium ion, and ammonium ion. Examples of the gelling aid containing potassium ion include potassium chloride, potassium bromide, potassium iodide, potassium acetate, and potassium phosphate. Examples of the gelling aid containing calcium ion include calcium chloride, calcium bromide, calcium iodide, calcium acetate, calcium lactate, and calcium phosphate. Examples of the gelling aid containing ammonium ion include ammonium chloride, ammonium bromide, ammonium iodide, ammonium acetate, and ammonium phosphate.

For example, when a kappa carrageenan is used as the gelling agent, it is preferable to use a gelling aid containing potassium ion, particularly potassium chloride. When gellan gum is used as the gelling agent, it is preferable to use a gelling aid containing calcium ion, particularly calcium lactate.

The content of the gelling aid in the composition for forming a film is preferably 10.0 parts by mass or less, more preferably from 0.25 to 5.0 parts by mass, relative to 100 parts by mass of HPMC polymers to be used in the composition for forming a film, from the viewpoint of preventing precipitation of the gelling aid.

The plasticizer is not particularly limited as long as it can be used for a pharmaceutical or food product. Examples of the plasticizer include triethyl citrate, triacetin, polysorbate 80 (Tween® 80), polyethylene glycol, and dioctyl sodium sulfosuccinate.

The content of the plasticizer in the composition for forming a film is preferably 30.0 parts by mass or less, more preferably from 0.1 to 15.0 parts by mass, relative to 100 parts by mass of HPMC polymers to be used in the composition for forming a film, from the viewpoint of strength of the film.

Examples of the pigment include titanium oxide, an aluminum lake, and an edible dye.

The content of the pigment in the composition for forming a film varies depending on the addition purpose such as light shielding and coloring. It is preferably 5.0 parts by mass or less, more preferably from 0.1 to 2.5 parts by mass, relative to 100 parts by mass of HPMC polymers to be used in the composition for forming a film, from the viewpoint of the strength of the film.

Examples of the flavoring agent include essential oils such as lemon oil, orange oil, peppermint, spearmint, and mentha oil; and synthetic flavors such as coffee flavor and yogurt flavor.

The content of the flavoring agent in the composition for forming a film is preferably 2.5 parts by mass or less, more preferably from 0.1 to 1.0 parts by mass, relative to 100 parts by mass of HPMC polymers to be used in the composition for forming a film, from the viewpoint of strength of the film.

Examples of the antifoaming agent include a silicone-based antifoaming agent, a sucrose fatty acid ester-based antifoaming agent, and a glycerin fatty acid ester-based antifoaming agent.

The content of the antifoaming agent in the composition for forming a film is preferably 2.0 parts by mass or less, more preferably from 0.1 to 1.0 parts by mass, relative to 100 parts by mass of HPMC polymers to be used in the composition for forming a film, from the viewpoint of film strength.

<Method for Producing Composition for Forming Film>

The composition for forming a film may be produced by, for example, the following methods.

A first method for producing a composition for forming a film comprises steps of: mixing the first, second and third HPMC polymers, a solvent of preferably from 85 to 98° C., a gelling agent and an optional additive (e.g., a gelling aid) other than the gelling agent with stirring at 300 to 600 rpm preferably at 80° C. or higher for 5 to 30 minutes to obtain a dispersion or solution; leaving the dispersion or solution to stand for defoaming without stirring preferably at 80° C. or higher for 20 to 60 minutes; and lowering a temperature of the defoamed dispersion or solution with stirring at 100 to 300 rpm to a temperature suitable for a film formation process, for example a temperature at which a mold pin is immersed in the production of a hard capsule. As a result, there can be produced a slurry-like composition for forming a film, wherein the composition contains a mixture of HPMC polymers dispersed or dissolved in a solvent. At the start of the step of leaving the dispersion or solution to stand for defoaming without stirring, the stirring is stopped preferably after confirming that the HPMC polymers are sufficiently dispersed or dissolved in the hot water.

A second method for producing a composition for forming a film comprises steps of; mixing first, second and third HPMC polymers and a solvent; cooling the resulting mixture to allow the HPMC polymers to be completely dissolved; and raising the temperature of the HPMC-dissolved mixture to a temperature suitable for a film formation process, wherein a gelling agent and an optional additive such as a gelling aid are added before or after the completion of raising the temperature of the HPMC-dissolved mixture. As a result, there can be produced a composition for forming a film, wherein the composition contains the HPMC polymers completely dissolved in the solvent. The first method for producing a slurry-like composition for forming a film is more preferable because the second method takes a long time to produce a composition for forming a film and lowers the productivity of the film formation.

<Application of Composition for Forming Film>

Examples of the application of the composition for forming a film include a film preparation, a hard capsule base material, and a coating base material. The composition is suitable for a hard capsule requiring high strength because the composition does not greatly impair the film strength.

The film may be produced by applying the film-forming composition on a base such as a glass plate using a bar coater or an applicator, or by immersing a base such as a capsule mold pin in the composition for forming a film and taking the base out of the composition; and then evaporating a solvent from the composition to form a film on the base. In other words, the film may be produced by a method comprising steps of: applying the film-forming composition on a base, removing a solvent from the composition to obtain a film on the base, and optionally detaching the film from the base.

Further, the film may be produced by a method comprising a step of spraying the composition onto a tablet or the like, while evaporating a solvent from the composition.

For example, 30 to 50 g of the film-forming composition having a gelling temperature (preferable gelling temperature of 50° C. or higher) which is equal to or higher than the gelling temperature of a gelling agent is flowed, while avoiding formation of foams, onto a glass plate which has been maintained horizontally and heated to a temperature lower than or equal to a gelling temperature of the gelling agent, and is subjected to casting with a YBA type baker applicator (produced by Yoshimitsu Seiki Co., Ltd.). Then, the composition on the glass plate is dried or solvent-removed at a temperature lower than or equal to the gelation temperature of the gelling agent, while keeping the glass plate horizontal, to form a film. It is dried or solvent-removed until the water content or solvent content of the film becomes 10% by mass or less, and then the film is detached from the glass plate. An optional and additional drying or solvent-removal may be carried out, for example, by placing the film on the glass plate in an air blow oven or the like prior to detachment of the film in order to further reduce the water content or solvent content of the film.

Further, a hard capsule may be produced by the method comprising steps: immersing a capsule mold pin of 5 to 20° C. in the composition for forming a film, taking the mold pin out of the composition, drying or solvent-removing the composition attached to the mold pin to form a film, detaching the film from the mold pin, cutting the detached film into pieces which are fitted into a capsule or capsules.

EXAMPLES

Hereinafter, the invention will be described more specifically with reference to Examples and Comparative Examples. It should not be construed that the invention is limited to or by Examples.

<Synthesis of HPMC>

Chips of wood pulp were immersed in a 49% by mass aqueous sodium hydroxide solution, and then an excess aqueous sodium hydroxide solution was removed to obtain alkaline cellulose. The obtained alkali cellulose was placed in a pressure-resistant reactor having a volume of 100 L. And 8.00 kg of methyl chloride and 1.72 kg of propylene oxide were added thereto for reaction, while raising the inside temperature of the reactor from 60 to 95° C. Then, the reaction product of HPMC was removed from the reactor, washed with hot water, and dried. Thereafter, impact pulverization was carried out to obtain HPMC.

Hydrochloric acid was sprayed onto the obtained HPMC and the resulting mixture was then transferred to a 2 L glass reactor. The glass reactor was heated in a water bath of 85° C., while being rotated, to carry out a depolymerization reaction for 80 minutes. As a result, there was obtained HPMC-IA-1 having a degree of substitution (DS) of the methoxy groups of 1.90, a molar substitution (MS) of the hydroxypropoxy groups of 0.25, and a viscosity at 20° C. of 3 mPa·s, as determined in a 2% by mass aqueous solution.

Various HPMC polymers were synthesized in the same manner as HPMC-IA-1.

A degree of substitution (DS) of the methoxy groups, a molar substitution (MS) of the hydroxypropoxy groups, and a viscosity at 20° C. as determined in a 2% by mass aqueous solution of each synthesized HPMC polymer are shown in Tables 1 and 2.

TABLE 1

HPMC in Group I

| type | No. | viscosity (mPa·s) | DS (—) | MS (—) |
|---|---|---|---|---|
| HPMC-IA | 1 | 3.0 | 1.90 | 0.25 |
|  | 2 | 4.5 | 1.90 | 0.24 |
|  | 3 | 4.9 | 1.90 | 0.25 |
|  | 4 | 6.0 | 1.90 | 0.24 |
|  | 5 | 7.2 | 1.89 | 0.25 |
|  | 6 | 9.2 | 1.89 | 0.25 |
|  | 7 | 17.0 | 1.90 | 0.25 |
|  | 8 | 32.6 | 1.90 | 0.25 |
|  | 9 | 48.0 | 1.89 | 0.25 |

TABLE 2

HPMC in Group II

| type | No. | viscosity (mPa·s) | DS (—) | MS (—) |
|---|---|---|---|---|
| HPMC-IIA | 1 | 3.3 | 1.46 | 0.25 |
|  | 2 | 4.6 | 1.46 | 0.25 |
|  | 3 | 6.4 | 1.46 | 0.25 |
|  | 4 | 18.6 | 1.46 | 0.25 |
| HPMC-IIB | 1 | 3.1 | 1.84 | 0.62 |
|  | 2 | 4.3 | 1.84 | 0.62 |
|  | 3 | 6.0 | 1.84 | 0.62 |
|  | 4 | 13.5 | 1.84 | 0.62 |

Example 1

The 20 g of HPMC-IA-1, 30 g of HPMC-IA-6, and 50 g of HPMC-IIA-3 were placed in a plastic bag, and mixed sufficiently to obtain a HPMC mixture, The 50 g of the HPMC mixture, 0.50 g of k-carrageenan (produced by Tokyo Kasei Kogyo Co., Ltd.), 0.25 g of potassium chloride (KCl) (produced by FUJI FILM Wako Pure Chemical Corporation), and 0.25 g of X-50-1105G (silicone-based antifoaming agent, produced by Shin-Etsu Chemical Co., Ltd.) were placed in a 300 mL of glass beaker, and subjected to addition of hot water of 90° C. to make a total amount of the resulting mixture to be 250 g. A top of the beaker was covered to prevent the evaporation of the solvent, and the resulting mixture was stirred at 400 rpm for 10 minutes in a hot water bath of 80° C. After confirming that the HPMC mixture was sufficiently dispersed in the hot water, stirring was stopped, and the mixture was left to stand at 80° C. for 30 minutes for defoaming. Thereafter, the beaker was moved into a hot water bath of 60° C., and the mixture in the beaker was stirred at 200 rpm, while lowering the temperature of the hot water bath by 2° C. per 30 minutes to obtain a film-forming composition of 50° C.

<Determination of a Viscosity at 20° C. of a 2% by Mass Aqueous Solution of a HPMC Mixture Used in the Composition for Forming a Film>

In Example 1, 4.0 g of the HPMC mixture obtained by mixing HPMC-IA-1, HPMC-IA-6 and HPMC-IIA-3 was dispersed in hot water of 90° C. in a glass beaker of 200 mL, and then stirred in a water bath of 5° C. for 30 minutes to prepare a 2% by mass aqueous solution of the HPMC mixture used in the composition for forming a film. Thereafter, a viscosity at 20° C. of a 2% by mass aqueous solution of the HPMC mixture used in the composition for forming a film was determined using a Ubbelohde type viscometer in accordance with the viscosity measurement by capillary viscometer of the General Tests in the Japanese Pharmacopoeia Seventeenth Edition.

<Determination of the Dispersion Viscosity of the HPMC Mixture Used in the Composition for Forming a Film>

Using an MCR301, which is a rheometer of Anton Paar GmbH, the dispersion viscosity of the HPMC mixture used in each composition for forming a film was determined, and the average value (n=3) of the dispersion viscosity was calculated. Each value of the dispersion viscosity obtained by the measurements is shown in Table 3.

<Production of Film>

Approximately 40 g of the film-forming composition having a temperature of 50° C. was poured, while avoiding formation of air foams, onto a glass plate being kept horizontal and having a temperature of 25° C. Then, the film-forming composition was subjected to manual casting using a YBA type baker applicator (produced by Yoshimitsu Seiki Co., Ltd.). Then, the glass plate was placed in a windless environment at 25° C., while being kept horizontally, and dried for 18 hours to form a film having a water content of 10% by mass or less. Thereafter, the film on the glass plate was further dried in an air blow oven at 80° C. for 1 hour, and then the film was detached from the glass plate to obtain a film having a thickness of 140±5 μm.

<Measurement of Film Strength>

The obtained film was cut into strips having 8 cm in length and 1 cm in width. Then the strips were left in an environment of 25° C. and 52 RH % for 3 days to prepare film test pieces having a water content of 6.5±0.5% by mass, as determined by a heating type moisture meter (MX-50 produced by A&D Company Limited).

A tensile test was carried out in a constant temperature and constant humidity machine (PR-3J being produced by ESPEC Corporation and having two φ15 cm operation ports on the front door) which was set to 25° C. and 52 RH %, by using a tabletop small tensile tester (MODEL-FTN-1-13A produced by Aikoh Engineering Co., Ltd.). To prevent slipping of the film, the test piece was fixed at the positions of 2 cm inside from the top and 2 cm inside from the bottom of the test piece by jigs having soft vinyl chloride sheets attached to flat chucks (MODEL-023 produced by Aikoh Engineering Co., Ltd.). The measurement was made under conditions of a fulcrum distance of 4 cm, a test velocity of 10 mm/min and a load cell rating of 500 N. The average value (n=10) of the film strength was calculated. The film strength obtained by the measurement is shown in Table 3.

<Measurement of Dissolution Time of Film>

For the evaluation of the solubility, a sample holder to be used was prepared based on the auxiliary tube described in the Disintegration Test of the Japanese Pharmacopoeia Seventeenth Edition, while referring to JP 2015-522614A, which was Japanese phase publication of WO 2014/018279 A1. The sample holder comprises a first sample holder body part 1, a first chrome steel ball 2, a sample holder lid 3, a silicone rubber packing 4, a second sample holder body part 6, and a second chrome steel ball 7.

The first sample holder body part 1 is a body part (inner diameter of 12 mm, outer diameter of 17 mm and length of 20 mm) of the auxiliary tube to be used in the Disintegration Test, and the sample holder lid 3 is obtained by removing a wire mesh from a lid (inner diameter of 12 mm, outer diameter of 17 mm and length of 4 mm) of the auxiliary tube to be used in the Disintegration Test. The second sample holder body part 6 is formed by combining a body part of the auxiliary tube to be used in the Disintegration Test with a lid (inner diameter of 12 mm, outer diameter of 17 mm, length of 4 mm) of the auxiliary tube, wherein the lid of the auxiliary tube is located on the bottom of the body part of the auxiliary tube, a hole in the side surface of the body part of the auxiliary tube is completely closed with a silicone rubber, and a wire mesh of the lid of the auxiliary tube is completely closed with a silicone rubber. The silicone rubber packing 4 having an inner diameter of 10 mm, an outer diameter of 14 mm and a thickness of 0.5 mm was used for the purposes of fixing the film and keeping an area of the film to be contacted with water constant during the test. The first chrome steel ball 2 having a weight of about 1.0 g and a diameter of about 6.35 mm (1/4 inches) was used for the purpose of reproducing the stress on the HPMC film in the stomach. The second chrome steel ball 7 having a weight of about 3.55 g and a diameter of about 9.53 mm (3/8 inches) was used for the purpose of preventing the second sample holder from floating during the test.

The dissolution time of the film was measured as follows. First, the obtained film was placed in an environment of 25° C. and 52 RH % for 3 days to have a water content of 6.5±0.5% by mass, as determined by a heating type moisture meter (MX-50 produced by A&D Company Limited). Thereafter, the film piece 5 having φ14 mm, obtained by punching the film, was placed between the second sample holder body part 6 containing the second chrome steel ball 7 and the silicone rubber packing 4, while keeping the surface exposed to air during formation of the film upward. Then, the film piece 5 was further fixed by the sample holder lid 3 by way of the silicone rubber packing 4.

Next, the first sample holder body part 1 and the sample holder lid 3 were fixed without a gap by an adhesive tape, the first chrome steel ball 2 was placed on the film, and the sample holder was set in the basket-rack assembly described in the Disintegration Test of the Japanese Pharmacopoeia Seventeenth Edition. And 1150 mL of pure water was placed in a low-sized beaker, the basket-rack assembly was placed in the low-sized beaker, and the dissolution time of the film was measured (n=6) by using a disintegration tester (NT-400 produced by Toyama Sangyo Co., Ltd.) under the conditions of a water temperature of 37±0.5° C. and raising and lowering the basket between the distance of 55 mm at a reciprocation rate of 15 cycles (reciprocations) per minute. The dissolution time of the film is defined as the elapsed time from the start of the test until the first chrome steel ball 2 enters into the second sample holder body part 6 through the film and contacts with the second chrome steel ball 7. The dissolution time of the film obtained by the measurement is shown in Table 3.

Considering that the film dissolves in the stomach, it is appropriate to perform the test using the first fluid (pH value of about 1.2) of the Disintegration Test. However, since the solubility of HPMC film is almost equivalent between pure water and the first fluid of the Disintegration Test, the film was evaluated using pure water.

Examples 2 to 12 and Comparative Examples 1 to 7

A composition for forming a film was produced in the same manner as in Example 1 except that the formulation was changed to each one of those shown in Tables 3 and 4. The produced composition was evaluated with respect to various physical properties in the same manner as in Example 1. Further, a film was prepared in the same manner as in Example 1, and subjected to measurements of the strength and dissolution time. The results are shown in Table 3 and 4.

Gellan gum (KELCOGEL AFT, produced by Sansho Co., Ltd.) as a gelling agent, and calcium lactate n-hydrate (Kanto Chemical Co., Ltd.) as a gelling aid were used in Examples 2 and 12 and Comparative Examples 2 and 7. No antifoaming agent was used in Examples 11 and 12 and Comparative Examples 6 and 7.

TABLE 3

| | composition for forming a film | | | | | |
|---|---|---|---|---|---|---|
| | HPMC | | | | | |
| | first (% by mass) | second (% by mass) | third (% by mass) | difference in viscosity between 1st and 2nd (mPa·s) | gelling agent (% by mass) | gelling aid (% by mass) |
| Example1 | HPMC-IA-1 (4.0) | HPMC-IA-6 (6.0) | HPMC-IIA-3 (10.0) | 6.2 | k-carrageenan (0.2) | KCl (0.1) |
| Example2 | HPMC-IA-1 (4.0) | HPMC-IA-6 (6.0) | HPMC-IIA-3 (10.0) | 6.2 | gellan gum (0.2) | Ca lactate (0.1) |
| Example3 | HPMC-IA-1 (8.0) | HPMC-IA-9 (2.0) | HPMC-IIA-3 (10.0) | 45.0 | k-carrageenan (0.2) | KCl (0.1) |
| Example4 | HPMC-IA-2 (3.8) | HPMC-IA-5 (6.2) | HPMC-IIA-3 (10.0) | 2.7 | k-carrageenan (0.2) | KCl (0.1) |
| Example5 | HPMC-IIA-1 (4.4) | HPMC-IIA-3 (5.6) | HPMC-IA-2 (10.0) | 3.1 | k-carrageenan (0.2) | KCl (0.1) |
| Example6 | HPMC-IIA-1 (8.0) | HPMC-IIA-4 (2.0) | HPMC-IA-2 (10.0) | 15.3 | k-carrageenan (0.2) | KCl (0.1) |
| Example7 | HPMC-IA-1 (9.7) | HPMC-IA-7 (5.3) | HPMC-IIB-4 (5.0) | 14.0 | k-carrageenan (0.2) | KCl (0.1) |
| Example8 | HPMC-IA-1 (11.7) | HPMC-IA-8 (3.3) | HPMC-IIB-4 (5.0) | 29.6 | k-carrageenan (0.2) | KCl (0.1) |
| Example9 | HPMC-IIB-1 (2.5) | HPMC-IIB-3 (2.5) | HPMC-IA-4 (15.0) | 3.0 | k-carrageenan (0.2) | KCl (0.1) |
| Example10 | HPMC-IIB-1 (3.7) | HPMC-IIB-4 (1.3) | HPMC-IA-4 (15.0) | 12.0 | k-carrageenan (0.2) | KCl (0.1) |
| Example11 | HPMC-IA-1 (4.0) | HPMC-IA-6 (6.0) | HPMC-IIA-3 (10.0) | 6.2 | k-carrageenan (0.2) | KCl (0.1) |
| Exampe12 | HPMC-IA-1 (4.0) | HPMC-IA-6 (6.0) | HPMC-IIA-3 (10.0) | 6.2 | gellan gum (0.2) | Ca lactate (0.1) |

| | composition for forming a film | | | | | | |
|---|---|---|---|---|---|---|---|
| | | | HPMC mixture | | | | film |
| | antifoaming agent (% by mass) | solvent (% by mass) | DS (—) | MS (—) | viscosity (mPa·s) | dispersion viscosity (mPa·s) | strength (N/mm$^2$) | dissolution time (min) |
| Example1 | X-50-1105G (0.1) | water (79.6) | 1.68 | 0.25 | 6.3 | 6150 | 55.7 | 13.0 |
| Example2 | X-50-1105G (0.1) | water (79.6) | 1.68 | 0.25 | 6.3 | 6150 | 58.9 | 12.0 |
| Example3 | X-50-1105G (0.1) | water (79.6) | 1.68 | 0.25 | 6.3 | 4850 | 56.1 | 11.8 |
| Example4 | X-50-1105G (0.1) | water (79.6) | 1.68 | 0.25 | 6.3 | 6150 | 57.8 | 12.7 |
| Example5 | X-50-1105G (0.1) | water (79.6) | 1.68 | 0.25 | 4.5 | 2800 | 53.2 | 10.6 |
| Example6 | X-50-1105G (0.1) | water (79.6) | 1.68 | 0.25 | 4.7 | 2850 | 53.4 | 9.9 |

TABLE 3-continued

| | | | | | | | | |
|---|---|---|---|---|---|---|---|---|
| Example7 | X-50-1105G (0.1) | water (79.6) | 1.88 | 0.34 | 6.5 | 4750 | 56.6 | 13.3 |
| Example8 | X-50-1105G (0.1) | water (79.6) | 1.88 | 0.34 | 6.8 | 3900 | 56.9 | 12.1 |
| Example9 | X-50-1105G (0.1) | water (79.6) | 1.88 | 0.34 | 5.6 | 3650 | 56.0 | 13.1 |
| Example10 | X-50-1105G (0.1) | water (79.6) | 1.88 | 0.34 | 5.7 | 3700 | 52.1 | 13.2 |
| Example11 | — | water (79.7) | 1.68 | 0.25 | 6.3 | 6150 | 55.4 | 12.9 |
| Exampe12 | — | water (79.7) | 1.68 | 0.25 | 6.3 | 6150 | 60.8 | 11.8 |

TABLE 4

| | composition for forming a film | | | | | |
|---|---|---|---|---|---|---|
| | HPMC | | | | | |
| | first (% by mass) | second (% by mass) | third (% by mass) | difference in viscosity between 1st and 2nd (mPa·s) | gelling agent (% by mass) | gelling aid (% by mass) |
| Comp. Ex. 1 | none | HPMC-IA-4 (10.0) | HPMC-IIA-3 (10.0) | — | k-carrageenan (0.2) | KCl (0.1) |
| Comp. Ex. 2 | none | HPMC-IA-4 (10.0) | HPMC-IIA-3 (10.0) | — | gellan gum (0.2) | Ca lactate (0.1) |
| Comp. Ex. 3 | HPMC-IA-2 (10.0) | none | HPMC-IIA-2 (10.0) | — | k-carrageenan (0.2) | KCl (0.1) |
| Comp. Ex.4 | none | HPMC-IIB-4 (5.0) | HPMC-IA-3 (15.0) | — | k-carrageenan (0.2) | KCl (0.1) |
| Comp. Ex. 5 | MC-IIB-2 (10.0) | none | HPMC-IA-4 (15.0) | — | k-carrageenan (0.2) | KCl (0.1) |
| Comp. Ex. 6 | none | HPMC-IA-4 (10.0) | HPMC-IIA-3 (10.0) | — | k-carrageenan (0.2) | KCl (0.1) |
| Comp. Ex. 7 | none | HPMC-IA-4 (10.0) | HPMC-IIA-3 (10.0) | — | gellan gum (0.2) | Ca lactate (0.1) |

| | composition for forming a film | | | | | | |
|---|---|---|---|---|---|---|---|
| | | | HPMC mixture | | | film | |
| | antifoaming agent (% by mass) | solvent (% by mass) | DS (—) | MS (—) | viscosity (mPa·s) | dispersion viscosity (mPa·s) | strength (N/mm$^2$) | dissolution time (min) |
| Comp. Ex. 1 | X-50-1105G (0.1) | water (79.6) | 1.68 | 0.25 | 6.3 | 6800 | 55.9 | 14.1 |
| Comp. Ex. 2 | X-50-1105G (0.1) | water (79.6) | 1.68 | 0.25 | 6.3 | 6800 | 56.6 | 13.2 |
| Comp. Ex. 3 | X-50-1105G (0.1) | water (79.6) | 1.68 | 0.25 | 4.6 | 3000 | 54.5 | 11.9 |
| Comp. Ex.4 | X-50-1105G (0.1) | water (79.6) | 1.88 | 0.34 | 6.7 | 5200 | 58.8 | 14.4 |
| Comp. Ex. 5 | X-50-1105G (0.1) | water (79.6) | 1.88 | 0.34 | 5.6 | 4050 | 56.1 | 14.0 |
| Comp. Ex. 6 | — | water (79.7) | 1.68 | 0.25 | 6.3 | 6800 | 54.5 | 13.8 |
| Comp. Ex. 7 | — | water (79.7) | 1.68 | 0.25 | 6.3 | 6800 | 58.8 | 13.9 |

In general, when the viscosity of HPMC becomes lower, or when the molar substitution (MS) of the hydroxypropoxy groups of HPMC becomes higher with the proviso of keeping the viscosity of HPMC constant, the solubility of the HPMC film becomes higher. Accordingly, the comparison and discussion should be made between Example and Comparative Example in which the viscosities and the substitution degrees of HPMC mixtures contained in the composition are almost the same. In addition, the comparison and discussion should be made between Example and Comparative Example in which the type of the gelling agent and the presence or absence of the antifoaming agent are the same because of elimination of their influence.

The results of each of Examples 1, 3 and 4 show the film strength of 55.7 N/mm$^2$ or higher, and the dissolution time shortened by 1.1 to 2.3 minutes and the dispersion viscosity reduced by 650 to 1950 mPa·s in comparison with those in Comparative Example 1.

The results of Example 2 show the film strength of 58.9 N/mm$^2$, and the dissolution time shortened by 1.2 minutes and the dispersion viscosity reduced by 650 mPa·s in comparison with those in Comparative Example 2.

The results of each of Examples 5 and 6 show the film strength of 53.2 N/mm² or higher, and the dissolution time shortened by 1.3 to 2.0 minutes and the dispersion viscosity reduced by 150 to 200 mPa·s in comparison with those in Comparative Example 3.

The results of each of Examples 7 and 8 show the film strength of 56.6 N/mm² or higher, and the dissolution time shortened by 1.1 to 2.3 minutes and the dispersion viscosity reduced by 450 to 1300 mPa·s in comparison with those in Comparative Example 4.

The results of each of Examples 9 and 10 show the film strength of 52.1 N/mm² or higher, and the dissolution time shortened by 1.2 to 1.3 minutes and the dispersion viscosity reduced by 350 to 400 mPa·s in comparison with those in Comparative Example 5.

The results of Example 11 show the film strength of 55.4 N/mm², and the dissolution time reduced by 0.9 minutes and the dispersion viscosity reduced by 650 mPa·s in comparison with those in Comparative Example 6.

The results of Example 12 show the film strength of 60.8 N/mm², and the dissolution time shortened by 2.1 minutes and the dispersion viscosity reduced by 650 mPa·s in comparison with those in Comparative Example 7.

As described above, it has been found that by combining the same members of the first and second HPMC polymers having the different viscosity values and the same or different substitution degrees with the different member of the third HPMC polymer selected from a Group different from the Group of the first and second HPMC polymers, a film having excellent solubility can be formed, while maintaining the film strength, and further, the dispersion viscosity of the composition for forming a film can be reduced.

EXPLANATION OF SYMBOLS

1: first sample holder body part
2: first chrome steel ball
3: sample holder lid
4: silicone rubber packing
5: film piece having ϕ14 mm
6: second sample holder body part
7: second chrome steel ball

The invention claimed is:

1. A composition for forming a film, the composition comprising:
   a first hydroxypropyl methyl cellulose polymer having a viscosity at 20° C. of from 2.5 to 4.5 mPa·s, as determined in a 2% by mass aqueous solution;
   a second hydroxypropyl methyl cellulose polymer having a viscosity at 20° C. of from 6.0 to 50.0 mPa·s, as determined in a 2% by mass aqueous solution;
   a third hydroxypropyl methyl cellulose polymer having a viscosity at 20° C. of from 4.5 to 15.0 mPa·s, as determined in a 2% by mass aqueous solution;
   a gelling agent; and
   a solvent;
   wherein the first hydroxypropyl methyl cellulose polymer is selected from three members:
      one member in Group I:
         hydroxypropyl methyl cellulose IA having a degree of substitution (DS) of methoxy groups of from 1.80 to 2.00 and a molar substitution (MS) of hydroxypropoxy groups of from 0.20 to 0.34, and
      two members both in Group II:
         hydroxypropyl methyl cellulose IIA having a degree of substitution (DS) of methoxy groups of from 1.10 to 1.60 and a molar substitution (MS) of hydroxypropoxy groups of from 0.10 to 0.33, and
         hydroxypropyl methyl cellulose IIB having a degree of substitution (DS) of methoxy groups of from 1.80 to 2.00, and a molar substitution (MS) of hydroxypropoxy groups of from 0.40 to 0.70,
   wherein the second hydroxypropyl methyl cellulose polymer is the same member as that of the first hydroxypropyl methyl cellulose polymer, provided that DS of the second hydroxypropyl methyl cellulose polymer may be the same as or different from DS of the first hydroxypropyl methyl cellulose polymer and MS of the second hydroxypropyl methyl cellulose polymer may be the same as or different from MS of the first hydroxypropyl methyl cellulose polymer, and wherein the third hydroxypropyl methyl cellulose polymer is selected from a member or members in a Group different from the Group of the first hydroxypropyl methyl cellulose polymer.

2. The composition for forming a film according to claim 1, wherein the first and second hydroxypropyl methyl cellulose polymers are the hydroxypropyl methyl cellulose IA and the third hydroxypropyl methyl cellulose polymer is the hydroxypropyl methyl cellulose IIA or IIB.

3. The composition for forming a film according to claim 1, wherein the first and second hydroxypropyl methyl cellulose polymers are the hydroxypropylmethylcellulose IIA or IIB, and the third hydroxypropyl methyl cellulose polymer is the hydroxypropyl methyl cellulose IA.

4. The composition for forming a film according to claim 1, wherein a mixture of the first, second and third hydroxypropyl methyl cellulose polymers has a degree of substitution (DS) of the methoxy groups of from 1.50 to 2.00, and a molar substitution (MS) of the hydroxypropoxy groups of from 0.20 to 0.55.

5. The composition for forming a film according to claim 1 a, wherein a mixture of the first, second and third hydroxypropyl methyl cellulose polymers has a viscosity at 20° C. of from 3.0 to 15.0 mPa·s, as determined in a 2% by mass aqueous solution.

6. The composition for forming a film according to claim 1, wherein the gelling agent is selected from the group consisting of kappa carrageenan, iota carrageenan, gellan gum, pectin, curdlan, agar and tamarind gum.

7. A film comprising:
   a first hydroxypropyl methyl cellulose polymer having a viscosity at 20° C. of from 2.5 to 4.5 mPa·s, as determined in a 2% by mass aqueous solution;
   a second hydroxypropyl methyl cellulose polymer having a viscosity at 20° C. of from 6.0 to 50.0 mPa·s, as determined in a 2% by mass aqueous solution;
   a third hydroxypropyl methyl cellulose polymer having a viscosity at 20° C. of from 4.5 to 15.0 mPa·s, as determined in a 2% by mass aqueous solution; and
   a gelling agent;
   wherein the first hydroxypropyl methyl cellulose polymer is selected from three members:
      one member in Group I:
         hydroxypropyl methyl cellulose IA having a degree of substitution (DS) of methoxy groups of from 1.80 to 2.00 and a molar substitution (MS) of hydroxypropoxy groups of from 0.20 to 0.34, and
      two members both in Group II:
         hydroxypropyl methylcellulose IIA having a degree of substitution (DS) of methoxy groups of from 1.10 to 1.60 and a molar substitution (MS) of hydroxypropoxy groups of from 0.10 to 0.33, and hydroxypropyl methyl cellulose IIB having a degree of substitution (DS) of methoxy groups of from 1.80 to 2.00 and a molar substitution (MS) of hydroxypropoxy groups of from 0.40 to 0.70, wherein the second hydroxypropyl methyl cellulose polymer is the same member as that of the first hydroxypropyl methyl cellulose polymer, provided that DS of the second hydroxypropyl methyl cellulose polymer may be the same as or different from the DS of the first hydroxypropyl methyl cellulose polymer and MS of the second hydroxypropyl methyl cellulose polymer may be the same as or different from the MS of the first hydroxypropyl methyl cellulose polymer, and wherein the third hydroxypropyl methyl cellulose polymer is selected from a member or members in a Group different from the Group of the first hydroxypropyl methyl cellulose polymer.

8. The film according to claim 7, wherein the gelling agent is selected from the group consisting of kappa carrageenan, iota carrageenan, gellan gum, pectin, curdlan, agar and tamarind gum.

* * * * *